(12) United States Patent
Lim et al.

(10) Patent No.: US 7,219,676 B2
(45) Date of Patent: May 22, 2007

(54) SUBSTRATE DETECTING APPARATUS

(75) Inventors: Moon-Taek Lim, Suwon (KR);
Eun-Sam Jung, Yongin (KR);
Ki-Ryong Choi, Suwon (KR)

(73) Assignee: Samsung Electronics Co., Ltd.,
Suwon-si, Gyeonggi-do (KR)

( * ) Notice: Subject to any disclaimer, the term of this patent is extended or adjusted under 35 U.S.C. 154(b) by 642 days.

(21) Appl. No.: 10/631,724

(22) Filed: Aug. 1, 2003

(65) Prior Publication Data

US 2004/0040587 A1    Mar. 4, 2004

(30) Foreign Application Priority Data

Sep. 3, 2002    (KR) ............... 10-2002-0052861

(51) Int. Cl.
*B08B 3/04* (2006.01)
(52) U.S. Cl. ............... 134/56 R; 134/113; 134/902
(58) Field of Classification Search ............... 134/113, 134/902, 56 R, 57 R
See application file for complete search history.

(56) References Cited

U.S. PATENT DOCUMENTS

| | | | | |
|---|---|---|---|---|
| 4,513,430 | A * | 4/1985 | Vora et al. ............... | 377/39 |
| 5,095,927 | A * | 3/1992 | Thompson et al. ...... | 134/102.1 |
| 5,206,627 | A * | 4/1993 | Kato ............... | 340/674 |
| 5,354,995 | A * | 10/1994 | Endo et al. ............... | 250/559.29 |
| 5,418,382 | A * | 5/1995 | Blackwood et al. ... | 250/559.36 |
| 5,640,440 | A * | 6/1997 | Kuno et al. ............... | 378/208 |
| 6,139,591 | A * | 10/2000 | Nakaura et al. ............... | 29/25.01 |
| 6,535,628 | B2 * | 3/2003 | Smargiassi et al. ......... | 382/149 |
| 6,665,583 | B2 * | 12/2003 | Kretz et al. ............... | 700/218 |
| 6,745,901 | B2 * | 6/2004 | Chen et al. ............... | 206/711 |

FOREIGN PATENT DOCUMENTS

| | | | |
|---|---|---|---|
| JP | 1-198742 | * | 9/1986 |
| JP | 1-295436 | * | 11/1989 |
| JP | 2-165650 | * | 6/1990 |
| JP | 3-297156 | * | 12/1991 |
| JP | 6-135506 | * | 5/1994 |
| JP | 11-214483 | * | 8/1999 |
| JP | 2000-124293 | | 4/2000 |
| JP | 2002096324 | * | 4/2002 |
| JP | 2002-170864 | * | 6/2002 |
| KR | 1999-0038610 | | 10/1999 |

OTHER PUBLICATIONS

European Patent Office 1 096 548 May 2001.*

* cited by examiner

*Primary Examiner*—Frankie L. Stinson
(74) *Attorney, Agent, or Firm*—Volentine & Whitt, PLLC

(57) ABSTRACT

A substrate cleaning apparatus includes a bath in the form of a vessel filled with a cleaning liquid, a substrate guide disposed on the bottom of the vessel and configured to support at least one substrate vertically, a first sensing unit for sensing the substrate(s) supported by the guide, and a second sensing unit for sensing substrates or remnants thereof disposed on the bottom of the vessel. The first sensing unit has sensor elements installed on the opposite sides of the vessel as situated across from one another. The second sensing unit has sensor elements installed on both sides and on the bottom of the vessel for detecting substrates or remnants from damaged substrates lying on the bottom of the process chamber.

19 Claims, 2 Drawing Sheets

SUBSTRATE DETECTING APPARATUS

BACKGROUND OF THE INVENTION

1. Field of the Invention

The present invention relates to an apparatus for detecting the presence or absence of a semiconductor wafer or other type of substrate, such as liquid crystal glass substrate, at a station in equipment for processing the substrate.

2. Description of the Related Art

A wet station typically comprises one and more baths filled with DI water or chemicals, and a substrate guide to supply a plurality of substrates to the baths. The substrates are cleaned while being moved sequentially among the baths. Also, a light-sensing unit is installed on each bath in order to detect the substrates that enter and leave the bath. The light sensing unit comprises a light emitting element and a light-receiving element disposed at opposite sides of the bath.

One conventional apparatus for detecting the semiconductor wafer in a semiconductor wet station is disclosed in Korean Laid-Open Utility Model No. 1999-0038610. The semiconductor wet station is constituted by a chemical bath and a de-ionized water bath to remove alien substances from the wafer. The semiconductor wet station also comprises a wafer detecting unit capable of detecting the wafers that enter and leave the chemical bath and the de-ionized water bath. The wafer detecting unit includes light-emitting and light-receiving elements disposed on the bottom of side walls of each bath.

These light-emitting and light-receiving elements of the wafer detecting apparatus are oriented to detect only the presence or absence of semiconductor wafers that are disposed upright at the bottom of the bath. That is, the conventional wafer detecting apparatus cannot detect for the presence of material lying on the bottom of the baths even though it is installed on a bottom portion of the bath.

Another conventional apparatus for detecting semiconductor wafers at a wet station is disclosed in Japanese Laid-Open Patent Publication No. 2000-124293. The wet station comprises a process vessel having transparent sidewalls. The apparatus for detecting semiconductor wafers includes a light sensor installed on the sidewalls of the process vessel, the sensor being oriented to detect for the presence of the upright wafers in the vessel.

However, the conventional wafer detecting apparatus can not detect wafers or damaged parts thereof that remain at the bottom of the process vessel. Accordingly, the wet station continues to operate even if wafers or damaged parts thereof remain at the bottom of the process vessel. Thus, wafers continue to be damaged and contaminated by remnants, thereby lowering the manufacturing yield.

SUMMARY OF THE INVENTION

An object of the present invention is to over come the above-described problems of the prior art. More specifically, an object of the present invention is to provide a substrate detecting apparatus having an ability to sense for the presence of material at the bottom of the process vessel.

Accordingly, the present invention provides a process vessel defining a process space therein, a substrate guide disposed on a bottom part of the process vessel and configured to support at least one substrate upright thereon as oriented vertically, a first sensing unit for detecting for the presence of substrates upright on the substrate guide, and a second sensing unit for detecting for the presence of damaged substrates or substrates lying on the bottom of the process vessel. The first sensing unit has sensor elements installed on the sides of the process vessel opposite one another. On the other hand, the second sensing unit has sensor elements installed on both sides and on the bottom of the process vessel, respectively.

The sensing elements of the first sensing unit preferably include at least one first light-emitting element positioned on one side of the process vessel for emitting light in a direction perpendicular to a substrate that is supported by the substrate guide, and at least one first light-receiving element positioned on another side of the process vessel to receive the light emitted from the first light-emitting element.

The sensing elements of the second sensing unit preferably include at least one second light-emitting element positioned on one side of the process vessel for emitting the light towards the bottom of the vessel at a predetermined angle oblique to a substrate that is supported by the substrate guide, a light reflector positioned on the bottom of the process vessel to reflect the light emitted from the second light-emitting element(s), and at least one second light-receiving element positioned on the other side of the process vessel for receiving the light reflected by the light reflector.

Preferably, the substrate guide and the process vessel are made of transparent materials such as quartz. In this case, the first and second light-receiving elements, and the light reflector can be installed on the outside of the process vessel.

BRIEF DESCRIPTION OF THE DRAWINGS

These and other objects, feature and advantages of the present invention will be better understood from the following detailed description thereof made in conjunction with the accompanying drawings, in which like reference numerals denote like elements, and in which.

DETAILED DESCRIPTION OF THE PREFERRED EMBODIMENTS

Figure 1:
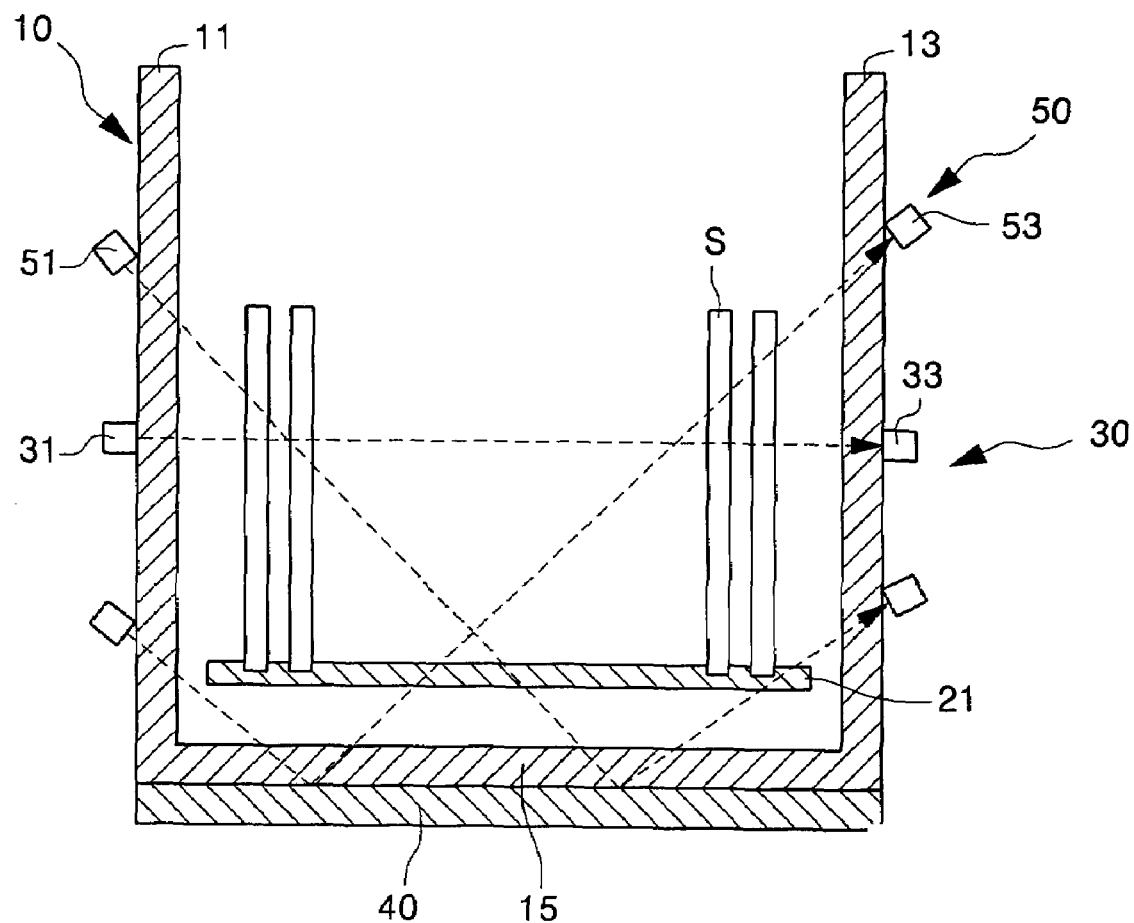
FIG. 1 is a schematic diagram of an apparatus for detecting the presence or absence of a substrate according to the present invention.

FIG. 1 schematically illustrates an apparatus for detecting the presence or absence of a substrate according to the present invention. The apparatus is installed on a process vessel 10 that defines a predetermined processing space in which at least one substrate is situated during the processing thereof. In this embodiment, the process vessel 10 is a bath wherein a plurality of substrates (S) are loaded on a bottom part of the process vessel 10 as oriented vertically by a substrate guide 21.

The apparatus for detecting the presence or absence of the substrate(s) includes a first sensing unit 30 installed on first and second sides 11 and 13 of the process vessel 10. The first sensing unit 30 includes at least one first light-emitting element 31 and at least one first light-receiving element 33. The first light-emitting element 31 is positioned on a first side 11 of the process vessel 10 for emitting light in a direction perpendicular to the substrates (S) that are situated upright at the bottom of the vessel 10. The at least one first light-receiving element 33 is positioned on the second side 13 of the process vessel 10 for receiving the light emitted from the first light-emitting element 31.

The apparatus for detecting the presence or absence of the substrate(s) also includes a second sensing unit 50 installed on the first and second sides 11, 13 of the process vessel 10, as well as on a bottom part 15 of the process vessel 10. The second sensing unit 50 includes at least one second light-emitting element 51, a light-reflecting element 40, and at least one second light-receiving element 53. The at least one the second light-emitting element 51 is positioned on the first side 11 of the process chamber 10 for emitting light at a predetermined angle that is oblique with respect to the substrates (S). The light-reflecting element 40 is positioned on the bottom part 15 of the process vessel 10 for reflecting the light emitted from the second light-emitting element 51. The at least one second light-receiving element 53 is positioned on the second side 13 of the process vessel 10 for receiving the reflected light from the light-reflecting element 40.

The process vessel 10 is preferably made of a transparent material, such as quartz, so that the first and second sensing units 30 and 50 may be disposed outside the process vessel 10. Accordingly, the first and second sensing units 30 and 50 will not be affected by environmental factors within the process vessel 10 such as those posed by the process gas, liquid, etc. The substrate guide 21 is also preferably made of a transparent material such as quartz. On the other hand, the light-reflecting element 40 has a surface that has a high degree of reflectance to the light emitted by the light-emitting elements 51 and preferably comprises a mirror.

Figure 2:
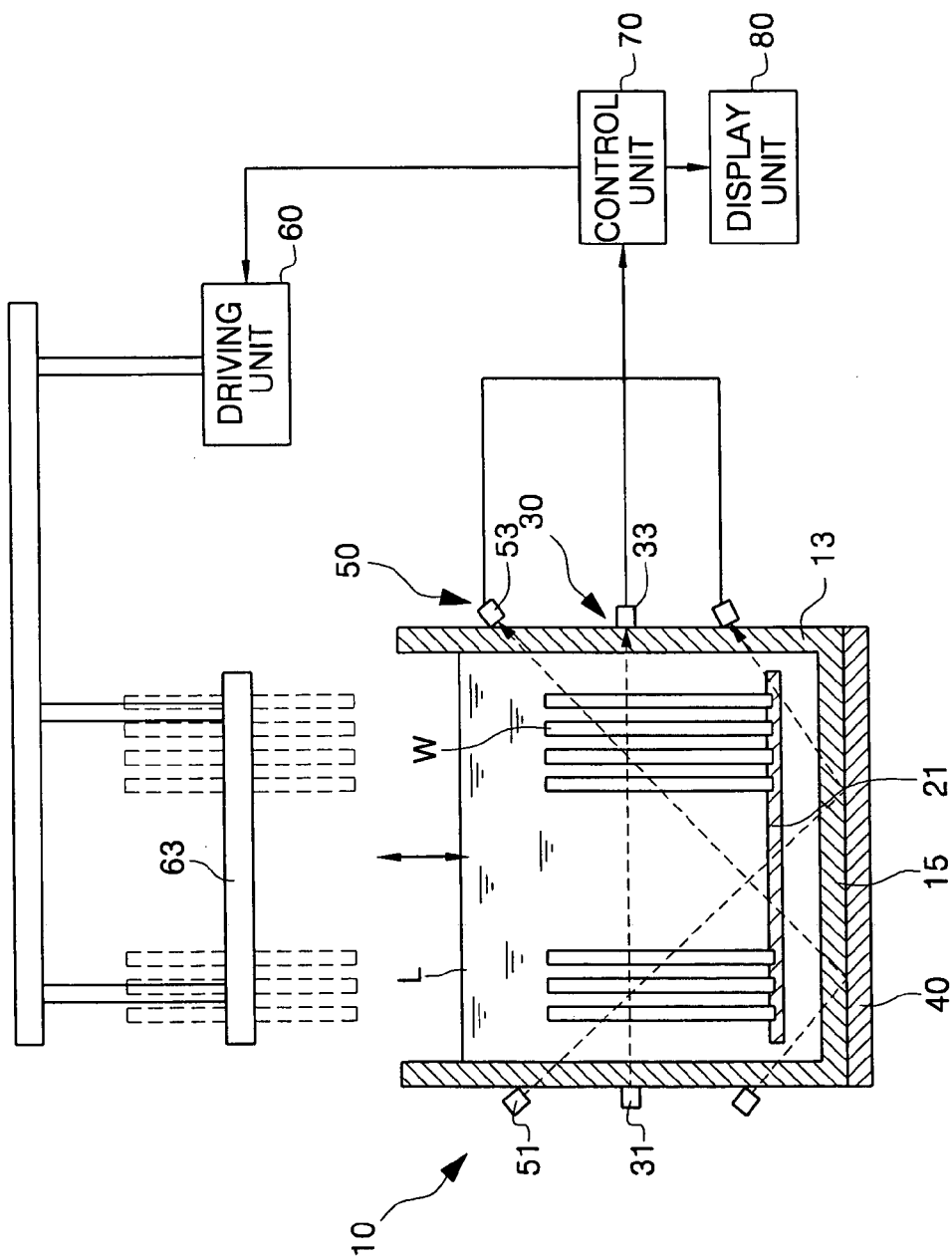
FIG. 2 is a schematic diagram of a wafer cleaning device employing the apparatus for detecting the presence or absence of a substrate according to the present invention.

FIG. 2 illustrates a semiconductor wafer cleaning device having the apparatus shown in FIG. 1. Referring to FIG. 2, the process chamber 10 is filled with a chemical or DI water (hereafter, referring to as cleaning liquid "L") to clean the substrates, shown here as semiconductor wafers W. A transfer arm 63 transfers the wafers W to the substrate guide 21. A driving unit 60 is operative to move the transfer arm 63 up and down and horizontally so that the transfer arm 63 can place the wafers W on the substrate guide 21 and later remove them from the process vessel 10. The driving unit 60 is connected to a control unit 70 so as to operate in response to directions issued by the control unit 70. The control unit 70 controls the driving unit 60 on the basis of signals from the first and second light-receiving elements 33 and 53.

For instance, the control unit 70 outputs an instruction that stops the driving unit 60 from operating when the signals from the first and second light-receiving elements 33 and 53 indicate an abnormal condition. A display unit 80 displays the existence of the abnormal condition. Thus, a technician can immediately recognize the abnormal condition from information provided on the display unit 80.

An operation of the semiconductor wafer cleaning device will now be described in more detail. First, the transfer arm 63 is moved up/down by the driving unit 60 to unload/load a plurality of wafers onto/from the substrate guide 21. At this time, the first sensing unit 30 detects for the presence/absence of the wafers W, whereby it can be determined as to whether the wafers W have entered/left the process vessel 10. For example, the light emitted from the first light-emitting element 31 is intercepted by the wafers W once one or more of the wafers W are placed upright on the substrate guide 21. At this time, the control unit 70 determines that the wafers have been transferred into the process vessel 10.

On the other hand, the light emitted from the first light-emitting element 31 is received by the first light-receiving element 33 when the wafers W are transferred out of the process vessel 10. At this time, the control unit 70 determines wafers are not in the process vessel 10, whereby the cleaning process is allowed to proceed.

However, the first sensing unit 30 can not detect wafers or remnants thereof lying on the bottom of the process vessel. If the cleaning process were allowed to continue in this state, the next batch of wafers would be damaged and/or contaminated by the remnants, whereby the manufacturing yield would be lowered.

This potential problem is obviated by the second sensing unit 50. More specifically, light emitted from the second light-emitting element(s) 51 to the light-reflecting element 40 is reflected by the light reflecting element 40 through the bottom 15 of the process vessel 10 and towards the second light-receiving element(s) 53. If wafers and/or remnants thereof remain on the substrate guide 21 or are present on the bottom 15 of the process vessel 10, i.e., if an abnormal condition exists in the vessel 10, the amount of light received by the second light-receiving element(s) 53 is different from the light received under normal conditions.

The control unit 70 determines whether an abnormal condition is prevailing in the process vessel by comparing the amount of light received by the light-receiving element(s) 53 with a value corresponding to the amount of light that is received under normal conditions. If the control unit 70 determines that an abnormal condition is prevailing in the process vessel 10, the control unit 70 outputs a driving stop signal to the driving unit 60 to stop the operation of the transfer arm 63, and displays the abnormal condition on display unit 80. Thus, a technician can take corrective measures to prevent more of the wafers from being damaged.

Finally, although the present invention has been particularly shown and described with reference to the preferred embodiments thereof, the present invention is not so limited. Rather, various changes in form and details may be made thereto without departing from the true sprit and scope of the invention as defined by the appended claims.

What is claimed is:

1. A combination of a process vessel having a bottom wall and a sidewall and defining a process space therein dedicated for use in accommodating substrates during their processing, a substrate guide disposed at the bottom of said process vessel and configured to support at least one substrate upright within the process vessel as oriented vertically within the vessel as spaced above the bottom wall of the process vessel, and a substrate detecting apparatus, wherein the substrate detecting apparatus comprises:

a first sensing unit having first sensor elements disposed on the sidewall of said process vessel, the first sensor elements being oriented and cooperative to detect for the presence of substrates that are supported upright by said substrate guide; and a second sensing unit having second sensor elements disposed on the sidewall and on the bottom wall of said process vessel, said second sensor elements being oriented and cooperative to detect for the presence of objects lying on the bottom wall of said process vessel, whereby substrates or remnants thereof which have fallen from the substrate guide and have come to rest on the bottom wall of the process vessel can be detected.

2. The combination of claim 1, wherein the first sensor elements include at least one first light-emitting element disposed on the sidewall of said process vessel and oriented to emit light in a direction perpendicular to a substrate that is supported upright by said substrate support, and at least one first light-receiving element disposed on said sidewall of the process vessel and positioned across the process space from each respective said light-emitting element so as to receive light emitted by the first light-emitting element.

3. The combination of claim 2, wherein the sensor elements of said second sensing unit include at least one second light-emitting element disposed on the sidewall of said process vessel and oriented to emit light in a direction oblique to a substrate that is supported upright by said substrate support and towards the bottom of said process vessel, a reflector disposed on the bottom wall of said process vessel so as to reflect light emitted from the at least one second light-emitting element, and at least one second light receiving element disposed on said sidewall of the process vessel and oriented to receive light reflected by said reflector.

4. The combination of claim 3, wherein said process vessel is of transparent material, and said first and second light-emitting elements, the first and second light-receiving elements, and said reflector are disposed on the outside of said process vessel.

5. The combination of claim 4, wherein the transparent material is quartz.

6. The combination of claim 3, wherein said reflector is a mirror.

7. The combination of claim 1, wherein the sensor elements of said second sensing unit include at least one second light-emitting element disposed on the sidewall of said process vessel and oriented to emit light in a direction oblique to a substrate that is supported upright by said substrate support and towards the bottom of said process vessel, a reflector disposed on the bottom wall of said process vessel so as to reflect light emitted from the at least one second light-emitting element, and at least one second light receiving element disposed on said sidewall of the process vessel and oriented to receive light reflected by said reflector.

8. The combination of claim 7, wherein said reflector is a mirror.

9. The combination of claim 1, wherein said substrate guide is of transparent material.

10. The combination of claim 9, wherein the transparent material is quartz.

11. The combination of claim 1, wherein said process vessel is filled with a chemical or deionized water.

12. Substrate cleaning apparatus comprising:
a bath comprising a process vessel having a bottom wall and a sidewall and defining a process space therein filled with a cleaning liquid;
a substrate guide disposed at the bottom of said process vessel and configured to support at least one substrate upright within the process vessel as oriented vertically within the vessel;
a first sensing unit having first sensor elements disposed on the sidewall of said process vessel, the first sensor elements being oriented and cooperative to detect for the presence of substrates that are supported upright by said substrate guide;
a second sensing unit having second sensor elements disposed on the sidewall and on the bottom wall of said process vessel, said second sensor elements being oriented and cooperative to detect for the presence of objects lying on the bottom of said process vessel, whereby substrates or remnants thereof lying on the bottom of the process vessel can be detected
a transfer arm configured to support a plurality of substrates;
a driving unit operatively connected to said transfer arm so as to move said transfer arm in and out of said process vessel to load and unload substrates onto and from said substrate guide; and
a controller operatively connected to said sensing units and to said driving unit so as to receive signals from said sensing unit and control said driving unit on the basis of said signals.

13. The substrate cleaning apparatus of claim 12, wherein the first sensor elements include at least one first light-emitting element disposed on the sidewall of said process vessel and oriented to emit light in a direction perpendicular to a substrate that is supported upright by said substrate support, and at least one first light-receiving element disposed on said sidewall of the process vessel and positioned across the process space from each respective said light-emitting element so as to receive light emitted by the first light-emitting element.

14. The substrate cleaning apparatus of claim 13, wherein the sensor elements of said second sensing unit include at least one second light-emitting element disposed on the sidewall of said process vessel and oriented to emit light in a direction oblique to a substrate that is supported upright by said substrate support and towards the bottom of said process vessel, a reflector disposed on the bottom wall of said process vessel so as to reflect light emitted from the at least one second light-emitting element, and at least one second light receiving element disposed on said sidewall of the process vessel and oriented to receive light reflected by said reflector.

15. The substrate cleaning apparatus of claim 14, wherein said process vessel is of transparent material, and said first and second light-emitting elements, the first and second light-receiving elements, and said reflector are disposed on the outside of said process vessel.

16. The substrate cleaning apparatus of claim 14, wherein said reflector is a mirror.

17. The substrate cleaning apparatus of claim 12, wherein the sensor elements of said second sensing unit include at least one second light-emitting element disposed on the sidewall of said process vessel and oriented to emit light in a direction oblique to a substrate that is supported upright by said substrate support and towards the bottom of said process vessel, a reflector disposed on the bottom wall of said process vessel so as to reflect light emitted from the at least one second light-emitting element, and at least one second light receiving element disposed on said sidewall of the process vessel and oriented to receive light reflected by said reflector.

18. The substrate cleaning apparatus of claim 17, wherein said reflector is a mirror.

19. The substrate cleaning apparatus of claim 12, wherein said substrate guide is of transparent material.

* * * * *